United States Patent [19]

Fosberg et al.

[11] 3,972,826

[45] Aug. 3, 1976

[54] FUEL MOISTURE ANALOG

[75] Inventors: Michael Allen Fosberg, Fort Collins, Colo.; James Wallace Lancaster, Star, Idaho; Mark Joseph Schroeder, Riverside, Calif.; Jerry D. Plunkett, Denver, Colo.

[73] Assignee: The United States of America as represented by the Secretary of Agriculture, Washington, D.C.

[22] Filed: Aug. 14, 1975

[21] Appl. No.: 604,860

[52] U.S. Cl. ............................. 252/408; 23/230 R; 73/73; 252/194; 252/455 R
[51] Int. Cl.² ..................... C09K 3/00; G01N 5/02
[58] Field of Search ............... 252/408, 194, 455 R, 252/463; 23/230 R; 73/73

[56] References Cited
UNITED STATES PATENTS

| | | | |
|---|---|---|---|
| 2,210,862 | 8/1940 | Tronstad | 252/194 |
| 2,255,041 | 9/1941 | Anderegg | 252/194 |
| 2,662,860 | 12/1953 | Engel et al. | 252/463 |

Primary Examiner—Benjamin R. Padgett
Assistant Examiner—David Leland
Attorney, Agent, or Firm—M. Howard Silverstein; David G. McConnell; Max D. Hensley

[57] ABSTRACT

This invention relates to the reproduction of all the essential moisture sorption characteristics of dead wildland fuels through use of an inorganic fuel moisture analog sensor. This inorganic fuel moisture analog sensor is calibrated to and reproduces all of the essential moisture sorption characteristics of dead wildland fuels without being subject to any of the undesirable characteristics associated with wood sensors. This analog is keyed to selectable response timelags, the size of these dead fuels, their water sorption processes, their radiation characteristics, and their thermal properties. This analog is fabricated from activated aluminum as the active material with calcium aluminate as the bonding agent.

2 Claims, 1 Drawing Figure

COMPARISON OF HUMIDITY RESPONSE OF A CALCIUM ALUMINATE-BONDED ACTIVATED ALUMINA (MC-7) WITH THAT OF WOOD (MC-1) WHEN CHANGES ARE BASED ON PERCENTAGE BY WEIGHT.

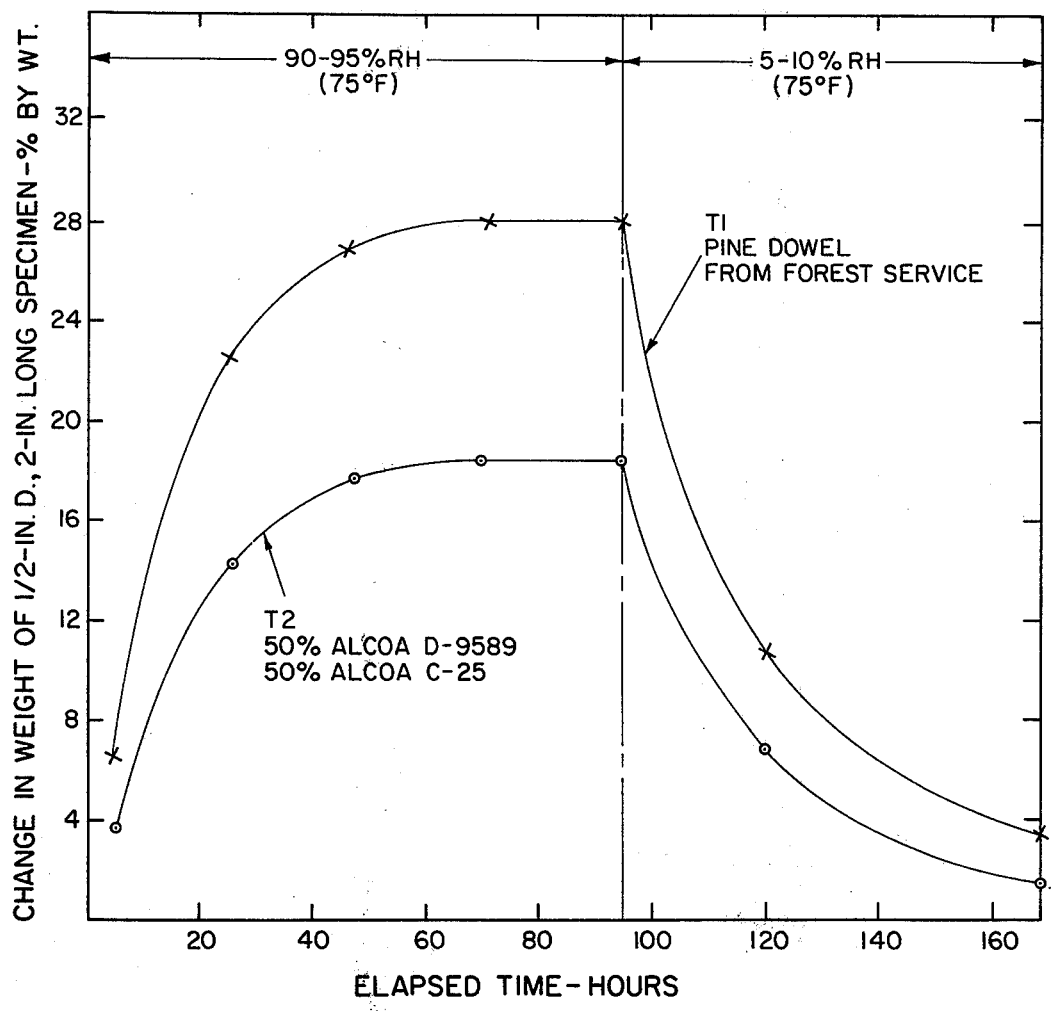
COMPARISON OF HUMIDITY RESPONSE OF A CALCIUM ALUMINATE-BONDED ACTIVATED ALUMINA (MC-7) WITH THAT OF WOOD (MC-1) WHEN CHANGES ARE BASED ON PERCENTAGE BY WEIGHT.

FUEL MOISTURE ANALOG

BACKGROUND OF THE INVENTION

1. Field of the Invention

This invention is designed to simulate moisture sorption processing in wildland fuels to provide moisture content values for fire danger and fire behavior predictions. This invention is keyed to fuel characteristics of moisture response timelag, surface area to volume ratio, shape factor, size, radiation properties, and water sorption characteristics with the additional advantage of not being subject to non-reproducibility which advantage eliminates calibration problems inherent in natural fuels.

2. Review of prior art

Numerous attempts have been made to simulate moisture contents of forest fuels through use of analog devices. Basswood slats have been used to estimate the moisture content of fine fuels; arrays of ½-inch diameter ponderosa pine dowels have been used to represent intermediate fuels; and arrays of 2-inch diameter ponderosa pine dowels have been used to represent heavy fuels. However, use of wood to indicate forest moisture has several deficiencies:

1. the response characteristics of wood are highly variable; they may vary as much as a factor of 10 between samples and as much as a factor of 2 between samples taken from the same piece of wood.
2. Exposure and aging produce discoloration, checking and splitting, and mass loss. Discoloration changes the radiation characteristics, and thus with exposure and aging a given set of environmental conditions will result in different fuel moistures on different dates. Checking and splitting, particularly on the ends, exposes more surface area for a given volume of fuel and also produces a shift in response characteristics. Loss of mass results in an absolute shift in calibration over a period of time.

Thus, the use of wood in a fuel moisture analog causes inaccuracies because of non-reproducible response characteristics between units, a change in response characteristics over time, and an absolute shift in calibration over time. These problems are not adequately countered by use of wood moisture meters. Thus, an object of this invention is to produce a sensor with reproducible response characteristics. A further object is to produce a sensor the response of which does not deteriorate with use and the passage of time. Achievement of these two objectives would permit a single calibration to be used for every unit rather than having to guess at the calibration of each unit as must be done presently.

The moisture content of the organic forest floor has been indicated by Duff hygrometers, but since these use wood as the basic sensor, they are subject to the same errors produced by response characteristics and variability in volumetric changes due to moisture content as the wood analogs noted above. Although the instrument could be calibrated more readily than could methods involving direct use of wood, it was not able to represent forest fuels other than the forest floor.

Computational analogs based on regression analysis of wood response to the environment, linear models, and direct use of the diffusion theory have been developed to represent forest fuel moisture, but these analogs are generally subject to errors introduced by the inability of calculations to include nonlinear interactive processes and by non-representative data, either by reduction of data to fuel level or by climatologically limited data.

Recently, a fuel moisture analog with an electrical readout was developed which implicitly represented several fuel sizes ranging from small fuels to large fuels, but this device has two major deficiencies: (1) the values of moisture content are not specifically keyed to forest fuel's response characteristic, and (2) the materials employed are inert.

It was an object of this invention to overcome the deficiencies of the previous art in the following respects: (1) the sensor is keyed directly to dead forest fuels and fire-danger rating; (2) the specified response characteristics can be maintained from unit to unit; (3) the materials are active and respond similarly to wood; (4) the geometric configuration of the analog can be prescribed so that its form is the same as the fuel it is representing; and (5) the analog has an electrical readout of the intra-pore humidity which represents the moisture content of the fuel.

SUMMARY OF THE INVENTION

The specific characteristics of wood that this invention is intended to simulate are the required moisture response timelags. Response times of 1, 10, and 100 hours correspond to fuels with radii of 0.11 to 0.16, 0.35 to 0.46, and 1.1 to 1.5 cm respectively for a large number of softwood species. These four response times represent respectively all dead fuels of less than 2 hours, 2 to 20 hours, 20 to 200 hours, and 200 to 2000 hours and thus include fuels of less than 0.21 cm, 0.16 to 0.65 cm, and 0.5 to 1.8 cm radius. The 10- and 100-hour timelag analogs fall within these ranges and thus preserve the required correspondence to wood. The 1-hour timelag analog slightly exceeds the typical range of wood sizes but the amount of excess is only 0.1 cm. However, by fabricating the 1-hour timelag analog in non-cylindrical form, the surface area to volume ratio will be increased and more closely conform to natural fine fuels such as conifer needles and grass and hardwood leaves as well as the fine branchwood. Timelags of 1, 10, 100, and 1000 hours are required under the current National Fire Danger Rating System, but the analogs can be produced to simulate any desired range of timelags; thus these specific timelags are not intended to represent exclusive timelag selections.

Natural wood has high solar radiation adsorption and high long-wave emissivity radiation characteristics; both are near 0.9. Both of these characteristics are preserved in the analog. Natural wood also has a high thermal diffusivity (K) as compared to its moisture diffusivity (V) with the ratio of K/V being about 1000. A similarly high ratio exists in the analog.

The water sorption characteristics of the analog and those of wood are also similar. At low moisture contents, water is in bonded form as well as in the free state. At high moisture contents, after all the bonding sites are used, the sorption process is by gradient-dependent diffusion through the porous capillary body. The calibration between wood and the analog is linear over the entire operating range.

In practice, the analogs of 1-, 10-, 100-, and 1000-hour timelags would be displayed in the field with two 1-hour elements, and one each of the 10-, 100-, and 1000-hour elements. One of the 1-hour elements would be buried in the organic soil layer to determine the litter and duff moisture content. The other 1-hour element along with the 10-, 100-, and 1000-hour elements would be exposed to the open air in a fashion similar to natural fuels. The exposed 1-hour element would also sense fuel temperature. Fire behavior and fire danger predictions are based on the integral mean moisture content of the analogs. This may be obtained by weighing the analogs, by embedding a humidity sensor within the analog, or by using the analog as a capacitor or resistor-type sensor.

The analogs are composed of activated alumina, Alcoa Chemicals Division formulation G220 or equivalent, bonded with calcium aluminate, Alcoa Chemicals Division formulation CA-20 calcium aluminate cement or equivalent.

The principal uses of the activated alumina are drying of gases and organic liquids, as a catalyst for dehydrogenation, and in chromatography; since all of these processes require a controlled and reproducible material, there should be minimal product variation from lot to lot thus providing uniform response of the analogs. The material as received is in the form of pelletized spheres approximately ⅛ inch in diameter. Because of their large size these spheres are not convenient for fabrication and are reduced in size by dry grinding to a size that will pass through size fraction 60 but be retained on 200 (U.S. Standard Sieves). This size is used merely for convenience of fabrication and is not, nor intended to be, exclusive. After size reduction, the material is dried and then placed in a sealed container to prevent moisture pick-up prior to weighing.

The main constituent of the calcium aluminate cement is $Ca\,Al_2\,O_4$ which reacts with water to give a gel structure with excellent bonding properties. This material is preferable to Portland cement for bonding the activated alumina because of better quality control in manufacturing, better flow properties after mixing with activated alumina, and less water required for mixing.

By weight the preferred ingredient proportions are 50 parts each of calcium aluminate and activated alumina and 61.2 parts of water; too much water causes a weak, porous structure and too little produces a mixture with poor forming properties and also causes the slurry to have poor flow properties after the vacuum treatment. In preparation for mixing the two constituents of the analogs, the correct amount of water is added to the activated alumina and allowed to remain until the material is saturated (approximately ½ hour). The calcium aluminate is then added and the mixture is stirred for 0.5 minute or until a homogeneous mix is achieved. This is a successful method but is not intended to be an exclusive method. Specimens are cast promptly after mixture.

Ordinary soda-lime-silica glass tubing is used as a mold material for convenience but is not the only type of mold that may be used. The advantages of glass tubing are that it is readily available in the sizes required, no lubricant or mold release compound that might contaminate the surface of the analog with a water repellent such as grease is required, and the analogs are readily removed by flame cracking the glass after completion of the curing cycle.

One method of casting involves introducing the slurry into a vibrating mold positioned at about a 45° angle; after filling, the mold is either vibrated for a short period or subjected to a vacuum of 0.5 to 1.0 torr for one to three minutes. An alternative method involves subjecting the slurry immediately before casting to a vacuum of 0.5 to 1 torr for 1 minute; after introduction of the slurry into the mold, the specimen is subjected to the vacuum procedure described in the first method. Both the vacuum treatments and the vibration of the mold are for the purpose of eliminating bubbles in the mixture.

To conform the analog to the solar adsorptivity of natural wood, a special black ceramic oxide pigment is added to the mixture before casting. Because a standard at the highest solar adsorptivity (lowest visible reflectivity) was chosen, correction factors for varying wood shades are necessary only in one direction.

After casting the analogs are cured in the glass tubing for 20 hours at 75°F with stoppers in the tube ends; then for 48 hours at 165°F standing in a closed container with water at the bottom and with the stoppers removed; then for 96 hours at 165°F in the same container with water removed.

After the glass molds are flame-cracked away from the specimens, the specimens are dried for 24 hours at 165°F.

Fire behavior and fire danger predictions are based on the integral mean moisture content of the analogs. This can be obtained by weighing the analogs or by embedding a humidity sensor within the analog or by using the analog as a capacitor- or resistor-type sensor.

DESCRIPTION OF THE PREFERRED EMBODIMENT

In the following data, T-1 represents pine dowels as currently used; T-2 represents an analog composed of 50 parts by weight each of calcium aluminate and activated alumina and 61.2 parts by weight of water. This specimen was manufactured as described above in the second method; that is, the vacuum treatment on the slurry was omitted although the specimen was so treated after casting; T-3 represents an analog composed by weight of 50 parts each of calcium aluminate and activated alumina and 66.7 parts water with vacuum treatment both before and after casting.

I

The uniformity of production of the analogs was illustrated by making three batches of the T-2 analog; six analogs were cast. Two batches of the T-3 analog were prepared from which four analogs were cast.

Five T-1 specimens were cut at random from a typical wood analog rack.

| Specimen Type | Dry Density (gm/cm³) |
|---|---|
| T-1 | 0.37 |
| T-1 | 0.37 |
| T-1 | 0.48 |
| T-1 | 0.47 |
| T-1 | 0.37 |
| T-2 | 1.37 |
| T-2 | 1.37 |
| T-2 | 1.37 |
| T-2 | 1.37 |
| T-2 | 1.37 |
| T-2 | 1.37 |
| T-3 | 1.29 |
| T-3 | 1.28 |
| T-3 | 1.29 |
| T-3 | 1.29 |

These determinations indicate that the uniformity of structure of the inorganic fuel analogs was superior to that of wood. Additionally it indicates that uniformity of structure is maintainable within the batch and reproducible between batches; thus one of the primary problems inherent in previously-used analogs is eliminated in this invention. Further, scratch hardness tests indicated that the analogs had a resistance to abrasion as good as or better than wood yet the specimens are capable of being cut with a hack saw. The strength properties of the specimens were found to be 1500 PSI in crush tests.

II

Two-inch long specimens of T-1 and several variants of the inorganic analogs were dried by heating in an oven for 24 hours at 165°F. Each was then weighed and then placed on a rack one inch above water in a 10-inch diameter desiccator where the relative humidity was approximately 90%. The specimens were weighed every 24 hours. The curves on the left portion of FIG. 1 were plotted from the results of the T-1 and T-2 specimens. The specimens were then placed in an 8-inch diameter desiccator containing Drierite ($CaSO_4$) which reduced the humidity in the desiccator below 10%. The Drierite was recharged as required to maintain the humidity at a low level. Weighings were again made at 24-hour intervals and the curves on the right side of FIG. 1 were plotted from the results of the T-1 and T-2 specimens. FIG. 1 indicates that a calibration of the analog is necessary to bring it into exact conformity with wood, but because of the uniformity of response of the analogs such calibration would only be required for the general type of manufacturing process used rather than a separate calibration curve for each analog as would be necessary for wood.

From an analysis of all the specimens tested, several conclusions were reached:

a. The cured calcium aluminate cement by itself acted as a highly effective desiccant when it was dried prior to testing. Although the total weight gains were comparable for specimens composed solely of calcium aluminate and those containing activated alumina, the saturation time for the former was considerably longer.

b. The water adsorption rate was dependent on the structure of the material with vacuum-cast, highly dense specimens adsorbing water much more slowly than the more porous specimens that were cast with no vacuum treatment.

c. Analog response was not particularly sensitive to the activated alumina content.

d. Analog response was not particularly sensitive to the grain size of the activated alumina.

e. On a weight basis, analogs prepared with high water contents adsorbed about the same amount of moisture as those prepared with low water contents.

f. Those specimens that gained weight most rapidly in high humidity lost weight most rapidly in low humidity, and those that gained weight most slowly in high humidity lost weight most slowly in low humidity.

g. The specimens consisting entirely of calcium aluminate cement lost weight at a rate similar to that at which they gained weight which indicates that the weight gain at high humidity was caused by adsorption of water into the fine pores and capillaries of the cement structure rather than by cement hydration.

h. The curves of FIG. 1 indicate that the response of the inorganic analogs corresponds very closely to that of wood. This response which is so closely keyed to wood is a significant improvement over presently-used inorganic analogs.

III

A purpose of this invention is to provide an analog that exhibits a reproducible response to the same humidity change for extended periods of time; as noted earlier, because of the wearing effect of weather and time on wood its response to a given set of conditions changes. To evaluate analog response to changes in humidity over a period of time similar specimens of T-1 and T-2 were prepared and cycled between low humidity and high humidity for a period of 20 days. The specimens were first placed in a desiccator with water for 24 hours, weighed, and then placed in the desiccator with Drierite for the same period before reweighing. The operation was repeated for a total of 10 wet-dry cycles. The following table lists the results.

| Cycle No. | Specimen Weight in High R.H. | | Specimen Weight in Low R.H. | |
|---|---|---|---|---|
| | T-1 gms. | T-2 gms. | T-1 gms. | T-2 gms. |
| 1 | 2.74 | 11.09 | 2.39 | 9.97 |
| 2 | 2.76 | 11.11 | 2.42 | 10.01 |
| 3 | 2.77 | 11.14 | 2.43 | 10.06 |
| 4 | 2.78 | 11.20 | 2.41 | 10.05 |
| 5 | 2.80 | 11.24 | 2.39 | 9.98 |
| 6 | 2.81 | 11.21 | 2.40 | 10.06 |
| 7 | 2.76 | 11.17 | 2.42 | 10.05 |
| 8 | 2.74 | 11.17 | 2.41 | 10.04 |
| 9 | 2.78 | 11.22 | 2.44 | 10.14 |
| 10 | 2.79 | 11.23 | 2.44 | 10.10 |
| Ave. | 2.773 | 11.178 | 2.415 | 10.046 |
| Std. Dev. | 0.022 | 0.049 | 0.017 | 0.051 |
| Coef. of Var.* | 0.79 | 0.44 | 0.70 | 0.49 |

*Standard deviation expressed as a percentage of the average.

The results of this experiment indicate that the analog response is largely consistent over time. Even under these controlled conditions, the response of the T-2 analog was significantly more stable than that of wood and an even greater record of consistency could be expected under use conditions where the wood specimen would be subject to discoloration, splitting, checking, and weight loss.

IV

Samples of both T-2 and T-3 were subjected to 10 cycles of freezing and thawing with no damage. In this test the specimens were immersed in water for 48 hours before initiating the test and again immersed in water after each freezing cycle. The specimens were cooled by placing them on an aluminum freezer shelf maintained at −5°F. The treatment time for both the freezing and thawing cycle always exceeded 4 hours. As noted above, no damage was observed in the specimens.

Having thus described our invention, we claim:

1. A method for preparing inorganic fuel moisture analog sensors that contain 50 parts by weight of activated alumina, 50 parts by weight of calcium aluminate and 61.2 parts by weight of water, which method consists of the following operational steps carried out in sequence:

a. drying a portion of activated alumina to produce a quantity of dry activated alumina of uniform moisture content;

b. mixing 61.2 parts by weight of water with 50 parts by weight of the dried and sized activated alumina of step (a) to produce an alumina saturated with respect to water;

c. mixing 50 parts by weight of calcium aluminate with the water-saturated alumina of step (b) to produce a homogeneous mixture;
d. introducing the homogeneous mixture of step (c) into preselected open top vibrating molds to produce a tightly packed homogeneous mixture essentially free from air bubbles;
e. subjecting the essentially air bubble free mixture of step (d) still in open top molds to a vacuum within the range 0.5 to 1.0 torr for periods of from 1 to 3 minutes, the longer intervals of time being employed with the lower vacuum range regions, to produce a mixture free of residual air bubbles;
f. closing the molds and curing the air bubble free mixture of step (e) first for a period of 20 hours at a temperature of 75°F and subsequently with molds open, for a period of 48 hours at a temperature of 165°F the latter curing period being carried out in an atmosphere saturated with respect to water;
g. finally equilibrating the mixture in open molds for 96 hours at a temperature of 165°F, the humidity being ambient, to produce the finished inorganic fuel moisture analog sensor.

2. The inorganic fuel moisture analog sensor produced by the method of claim 1.

* * * * *